(12) United States Patent
Peng et al.

(10) Patent No.: US 12,226,080 B2
(45) Date of Patent: Feb. 18, 2025

(54) ENDOSCOPE HOST AND ENDOSCOPE DEVICE FOR INTELLIGENTLY DETECTING ORGANS

(71) Applicant: NeoPed Technology Co., Ltd., Hsinchu County (TW)

(72) Inventors: Hui-Chun Peng, Hsinchu County (TW); Chih-Peng Lin, Hsinchu County (TW)

(73) Assignee: NeoPed Technology Co., Ltd., Hsinchu County (TW)

( * ) Notice: Subject to any disclaimer, the term of this patent is extended or adjusted under 35 U.S.C. 154(b) by 435 days.

(21) Appl. No.: 17/770,290

(22) PCT Filed: Oct. 21, 2019

(86) PCT No.: PCT/CN2019/000199
§ 371 (c)(1),
(2) Date: Apr. 20, 2022

(87) PCT Pub. No.: WO2021/077240
PCT Pub. Date: Apr. 29, 2021

(65) Prior Publication Data
US 2023/0047334 A1    Feb. 16, 2023

(51) Int. Cl.
*A61B 1/00* (2006.01)
*A61B 1/04* (2006.01)
*G16H 40/63* (2018.01)

(52) U.S. Cl.
CPC .......... *A61B 1/04* (2013.01); *A61B 1/000094* (2022.02); *A61B 1/000096* (2022.02); *A61B 1/00052* (2013.01); *A61B 1/00059* (2013.01); *A61B 1/00124* (2013.01); *A61B 1/00128* (2013.01); *G16H 40/63* (2018.01)

(58) Field of Classification Search
CPC ................ A61B 1/04; A61B 1/000094; A61B 1/000096; A61B 1/00052; A61B 1/00059; A61B 1/00124; A61B 1/00128; A61B 1/00009; G16H 40/63
USPC ......................................................... 600/103
See application file for complete search history.

(56) References Cited

U.S. PATENT DOCUMENTS 6,293,910 B1 *   9/2001   Yamakita ............. A61B 1/0623
                                                         600/110
2013/0131579 A1 *   5/2013   Mantell ..................... G01L 9/02
                                                         604/23

* cited by examiner

*Primary Examiner* — Timothy J Neal
*Assistant Examiner* — James Edward Boice
(74) *Attorney, Agent, or Firm* — Fei-hung Yang

(57) ABSTRACT

Disclosed are an endoscope host and an endoscope device for intelligently detecting organs including a main body having a connection channel for inserting an endoscope tube, and a drive connection part and an electrical connection identification part have first electrical connection points and second electrical connection point respectively. When the endoscope tube is inserted into the connection channel, the endoscope tube is electrically conducted with the first electrical connection point and the second electrical connection point to generate a driving signal and a type signal respectively. An organ identification unit is provided for storing an organ comparison table and comparing the type signal with the organ comparison table to obtain the organ type of the endoscope tube and generate an execution signal. A processing unit is installed in the main body for receiving the driving signal and the type signal and displaying a result image according to the execution signal.

12 Claims, 15 Drawing Sheets

ENDOSCOPE HOST AND ENDOSCOPE DEVICE FOR INTELLIGENTLY DETECTING ORGANS

BACKGROUND

Technical Field

The present disclosure relates to the field of medical endoscopes, and more particularly to an endoscope applicable for various types of medical treatments and capable of automatically executing corresponding image detection of an endoscope host and an endoscope device for intelligently detecting organs.

Description of Related Art

In some medical treatment areas such as gastroenterology, ENT, obstetrics and gynecology, urology, etc., endoscopic examination is generally used as a diagnosis and treatment method for determining symptoms, in which an endoscope is used to examine a patient's organs. However, it is necessary to design the endoscopic catheter with a corresponding specification and size to improve the detection accuracy and safety of use according to different parts of the human body.

In the current endoscope device, a control host and an endoscopic catheter are designed as "one-to-one" parts; in other words, the endoscopic catheter can only be assembled to the corresponding control host for use. For example, the endoscope used for examining stomach can only be assembled to a gastroscope for its operation and use on the control host of the gastroscope. When such endoscopic catheter is assembled to other control hosts of other endoscopes, it cannot be driven at all, because each endoscope catheter and its corresponding control host have their compatible electrical structures. Once if a type A endoscopic catheter is installed to a type B control host, the two will not be compatible with each other and will not work. Therefore, it is necessary to purchase the corresponding control host and endoscope catheter for the examination of different organs, thereby greatly increasing the cost of equipment. In some medical treatments, the diagnosis and treatment process does not just examine a single part of the patient's body only. For example, it may be necessary to examine the patient's intestine and stomach separately in gastroenterology, and intestines can be divided into duodenum, colon, sigmoid colon, small intestine or large intestine and other parts, and each part requires the specification of its corresponding endoscopic catheter for detection, and each of the aforementioned endoscope catheters must be equipped with a corresponding control host before it can be used. Therefore, medical personnel must find the endoscopic catheter corresponding to the control host, or the control host corresponding to the endoscopic catheter before they can be assembled and used for the examination, thereby causing extreme inconvenience.

In view of this problem, the discloser based on years of experience in the related industry to conduct research and experiment, and finally developed an endoscope host and an endoscope device for intelligently detecting organs to overcome the drawbacks of the traditional endoscopic examination.

SUMMARY

Therefore, it is a primary objective of the present disclosure to provide an endoscope host and an endoscope device for intelligently detecting organs, which allow a control host to automatically detect an endoscope tube type, and achieve a "one-to-many" compatible effect with various different endoscopes, thereby effectively reducing the testing equipment cost, and greatly improving convenience of examination.

To achieve the foregoing and other objectives, the present disclosure discloses an endoscope host for intelligently detecting organs, including: a main body, having a connection channel, a connecting hole formed on an external surface of the main body, and the connection channel and the connecting hole communicating to each other and provided for inserting an endoscope tube from the connecting hole into the connection channel; an electrical connection driving part, installed in the main body, and having a plurality of first electrical connection points correspondingly disposed the plurality of first electrical connection points in the connection channel; an identification electrical connection part, installed in the main body and configured to be adjacent with the electrical connection driving part, and the identification electrical connection part having a plurality of second electrical connection points correspondingly disposed in the connection channel; an organ identification unit, installed in the main body and telecommunicatively connected to the identification electrical connection part, and the organ identification unit having an organ comparison table stored therein, wherein when the endoscope tube is inserted from the connecting hole into the connection channel, the endoscope tube and the plurality of first electrical connection points are electrically conducted with each other to generate a driving signal, and the endoscope tube and a part or all of the second electrical connection points are electrically conducted with each other to generate a type signal; and the organ identification unit compares the received type signal with the organ comparison table to determine the organ type corresponding to the endoscope tube, and output an execution signal accordingly; and a processing unit, installed in the main body and telecommunicatively connected to the organ identification unit and the electrical connection driving part, such that after the execution signal and the driving signal are received, a result image is displayed according to the execution signal.

This disclosure also discloses an endoscope device for intelligently detecting organs, and the endoscope device includes: at least one endoscope tube, having a shooting end and a connecting end, and the connecting end having a plurality of third electrical connection points and at least one fourth electrical connection point, and the plurality of third electrical connection points and the plurality of fourth electrical connection points being arranged linearly; and in the endoscope host as described above, when the connecting end of the endoscope tube is inserted into the connecting hole, the plurality of third electrical connection points are provided for forming an electrical conduction with the plurality of first electrical connection points, and the fourth electrical connection point are provided for forming an electrical conduction with the second electrical connection point.

DESCRIPTION OF THE EMBODIMENTS

This disclosure will now be described in more detail with reference to the accompanying drawings that show various embodiments of this disclosure.

Figure 1A:
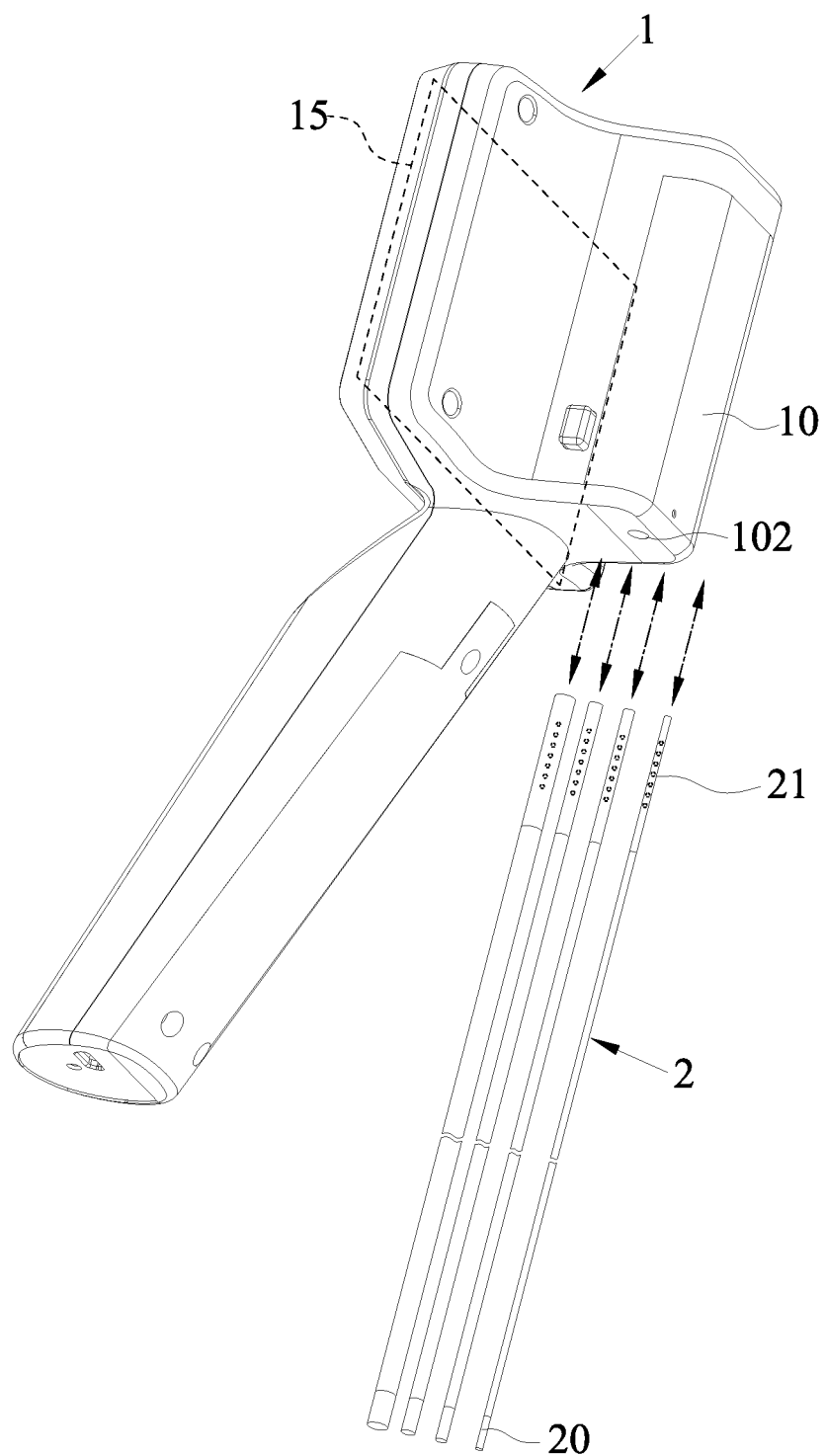
FIG. 1A is a schematic perspective view of an endoscope host and an endoscope tube in accordance with a preferred embodiment of this disclosure.

With reference to FIGS. 1A~3 for the perspective view of an endoscope host and an endoscope tube, the partial exploded view of the endoscope host and the endoscope tube, the first partial perspective view of the endoscope host, the schematic block diagram, the second partial perspective view of the endoscope host, the partial perspective view of the endoscope host and the endoscope tube, and the schematic views showing the applications of the endoscope host installed with an endoscope tube of different diameter in accordance with a preferred embodiment of this disclosure respectively, this disclosure discloses an endoscope host and an endoscope device for intelligently detecting organs, and the endoscope host 1 will be described first. The endoscope host 1 includes a main body 10, an electrical connection driving part 11, an electrical connection identification part 12, an organ identification unit 13 and a processing unit 14. The main body 10 has a connection channel 101 and a connecting hole 102 formed on an external surface of the main body 10, and the connection channel 101 and the connecting hole 102 are communicated with each other and provided for inserting an endoscope tube 2 from the connecting hole 102 into the connection channel 101. Preferably, the main body 10 has a connection part, and the connection channel 101 and the connecting hole 102 are disposed at the connection part and configured to be corresponsive to the connection channel 101 which is disposed inside the main body 10, and the connecting hole 102 is situated at a structural status at the external surface of the main body 10, and the connection part can be integrally formed or separable. When the connection part is separable, a press switch can be installed at a position of the main body 10 corresponding to the connection part for controlling the fixed status of the connection part. The electrical connection driving part 11 is installed in the main body 10 and has a plurality of first electrical connection points 111 disposed in the connection channel 101. The electrical connection identification part 12 is installed in the main body 10 and configured to be adjacent to the electrical connection driving part 11, and the electrical connection identification part 12 has a plurality of second electrical connection points 121 disposed in the connection channel 101, wherein the electrical connection driving part 11 and the electrical connection identification part 12 can be integrally formed or separately installed. For example, the electrical connection driving part 11 and the electrical connection identification part 12 are two parts of the same substrate, or the electrical connection driving part 11 and the electrical connection identification part 12 are two different substrates connected or configured to be adjacent with each other. FIG. 2A shows that the electrical connection driving part 11 and the electrical connection identification part 12 are two parts of the same circuit substrate and in the status of being configured to be adjacent to each other. It is noteworthy that this figure only shows a preferred embodiment, but not the actual structure. When the endoscope tube 2 is inserted from the connecting hole 102 into the connection channel 101, the endoscope tube 2 is electrically conducted with all of the first electrical connection points 111 to generate a driving signal, and the endoscope tube 2 is electrically conducted with a part or all of the second electrical connection points 121 to generate a type signal; for example, it is just conducted with one of the second electrical connection points 121, or it is conducted with all of the second electrical connection points 121. The organ identification unit 13 is installed in the main body 10 and provided for storing an organ comparison table and comparing the received organ signal with the organ identification unit 13 to determine an organ type of the endoscope tube 2 and output an execution signal according to the organ type. Wherein, the intelligent detection of organs refers to the detection of any two organs selected from the group consisting of large intestine (1111), duodenum (1101), colon (1110), sigmoid colon (1011), bronchus (1010), small intestine (1001), ureter (1000), bladder (0111), nose (0101), throat (0100), esophagus (0011), gallbladder (0010), stomach (0001), and joint (0000). The numbers in parentheses above represent the random coded data of the corresponding organs in the organ comparison table. The processing unit 14 is installed in the main body 10 and telecommunicatively connected to the organ identification unit 13 and the electrical connection identification part 12, and provided for displaying a result image according to the execution signal after the execution signal and the driving signal are received. In other words, after the processing unit 14 receives the execution signal, the name or image of an organ corresponding to the endoscope tube 2 is displayed and provided for immediately identifying the organ type corresponding to the endoscope tube 2 that is inserted into the main body 10. For example, if the endoscope tube 2 is a stomach probe, after the processing unit 14 receives the execution signal, the word "stomach" or the image of the stomach can be displayed. With the installation of the electrical connection identification part 12, the type signal can be generated according to the conduction status of the plurality of second electrical connection points 121, and compared with the stored organ comparison table by the organ identification unit 13, so as to know what organ is tested by the corresponding inserted endoscope tube 2, and then the processing unit 14 displays the corresponding result image, and this application can avoid incorrect installation that leads to delays of detection and causes inconvenience. In FIG. 1A, the endoscope host 1 is assembled to various different endoscope tubes 2 for use, and capable of surely detecting the corresponding organ type of the endoscope tube 2.

In a preferred implementation mode, there are three first electrical connection points 111, and at least four second electrical connection points 121. In this embodiment, three first electrical connection points 111 and four second electrical connection points 121 are used for illustrating this disclosure, and the plurality of first electrical connection points 111 and the plurality of second electrical connection points 121 have an elastic electrical contact structure to facilitate improving the pressing and fixing effect of the endoscope tube 2 by the elastic acting force when the endoscope tube 2 is electrically conducted. In a preferred implementation mode, the driving signal can be a binary 3-bit code, and the type signal can be a corresponding binary 4-bit code, wherein the driving signal has a code of 111, and the type signal has a code equal to 1 corresponding to the bit code of the second electrical connection point in a conducted status, a code equal to 0 corresponding to the bit code of the second electrical connection point in a non-conducted status. In other words, after the endoscope tube 2 is put into the connection channel 101 from the connecting hole 102 and contacted with the electrical connection driving part 11 and the electrical connection identification part 12, at least one of the second electrical connection points 121 will be in a conducted status. At this time a code is formed according to the arranged position of the conducted second electrical connection point 121. For example, when the first of the second electrical connection points 121 and the third of the second electrical connection points 121 are in the conducted status, the code of the generated identification signal is 1010, and when the first of the second electrical connection points 121 and the fourth of the second electrical connection points 121 are in the conducted status, the code of the identification signal is 1001, and the same rule applies to other remaining possible codes. The organ comparison table includes a plurality of encoded data and a plurality of corresponding organ data provided for the organ identification unit 13 to read the type signal and compare the code of the type signal with the plurality of encoded data to obtain the corresponding organ data, so as to generate the execution signal. For example, when the value of the encoded data is 0001, the organ data are corresponsive to stomach, and when the value of the encoded data is 1010, the organ data are corresponsive to bronchus, and after the organ identification unit 13 obtains the corresponding organ data, the corresponding execution signal is generated. Of course, the driving signal and the type signal can be set by the aforementioned codes, or the driving signal is a binary code with more than three bits and the type signal is a binary code with more than four bits.

In a preferred embodiment, the part of the connection channel 101 corresponding to the electrical connection driving part 11 and the electrical connection identification part 12 is a crescent tubular groove. In other words, the part of the connection channel 101 corresponding to the electrical connection driving part 11 and the electrical connection identification part 12 is an open groove, and the remaining part is an enclosed tubular structure. With this structural design, an arc contact area relative to the endoscope tube 2 is formed when the endoscope tube 2 is inserted into the connection channel 101, and the larger the diameter of the endoscope tube 2, the larger the area of the arc contact area, so that when the connection channel 101 is a crescent tubular groove, an appropriate pressing and fixing effect can be achieved for the endoscope tubes 2 of different diameters. Regardless of the diameter of the endoscope tube 2, the crescent structure provides an effect of uniformly applying pressure at the end of the endoscope tube 2 to avoid the problem of having rotational offset of the endoscope tube 2 after the endoscope tube 2 is inserted, so as to achieve the secured positioning effect. In FIG. 2C, when the endoscope tube 2 with a relatively larger diameter is inserted into the connection channel 101, the crescent tubular groove structure at the top side, the connection channel 101 and the endoscope tube 2 will form an arc contact area with a relatively area which is pressed by them, and another side of the endoscope tube 2 is pressed and clamped in another direction in response to the plurality of first electrical connection points 111 or the plurality of second electrical connection points 121 to stabilize the endoscope tube 2. With reference to FIG. 2C for the schematic view showing the installation status of the endoscope tube 2a with a relatively smaller diameter, after the endoscope tube 2 with a relatively smaller diameter is inserted into the connection channel 101, an arc contact area with a relatively smaller area will be formed in response to the crescent tubular groove structure, the connection channel 101 and the endoscope tube 2, which is pressed by them, and the plurality of first electrical connection points 111 or the plurality of second electrical connection points 121 on another side will press the endoscope tube 2. It can be seen from the above that regardless of the diameter, the endoscope tubes 2 of different diameters can be assembled with the endoscope host 1 for use. Regardless of the endoscope tube 2 with a large or small diameter, an arc contact area will be formed in response to the crescent structure of the connection channel 101, and a pressing and fixing effect will be produced in response to the first or second electrical connection point. In addition, the electrical connection identification part 12 further includes a signal path identification confirmation key 122 configured to be corresponsive to an end of the connection channel 101, and after the signal path identification confirmation key 122 is pressed by the endoscope tube 2 to achieve an electrical conduction, the plurality of first electrical connection points 111 and the plurality of second electrical connection points 121 are electrically conducted with the endoscope tube 2. The signal path identification confirmation key 122 is preferably a micro switch, and after the endoscope tube 2 touches and presses the signal path identification confirmation key 122, an electrical conduction is achieved in response to the touching and pressing operation, and thus can confirm whether the endoscope tube 2 inserted from the connecting hole 102 into the connection channel 101 is inserted in a correct direction or in a secured manner to avoid a short circuit of the plurality of first electrical connection points 111 and the plurality of second electrical connection points 121 with the endoscope tube 2 which may cause damages to the components when the endoscope tube 2 is incorrectly inserted into the connection channel 101. Therefore, the signal path identification confirmation key 122 can serve as a foolproof positioning structure to prevent wrong detections that lead to the occurrence of dangerous detection situations. For example, if the endoscope tube 2 is incompletely inserted into the connection channel 101 and misaligned during a connection, the endoscope tube 2 will be electrically conducted with the plurality of first electrical connection points 111 and the plurality of second electrical connection points 121, which may cause a misjudgement of the codes, such as the endoscope tube 2 originally intended to be used as a gastroscope for stomach examination becomes an urethroscope for urethral examination due to the misaligned connection and this may lead to a misjudgement by an examiner, and the endoscope tube 2 may be applied to a wrong examined part. The wrong detection as described in the example above may make the examiner to use the gastroscope for urethral examination, thereby resulting in a visceral or organ burst and hemorrhage, or even death. The signal path identification confirmation key 122 adopted in this disclosure is provided for detecting the endoscope tube 2 more accurately, eliminating misjudgements, and preventing possible dangerous situations.

In order to facilitate viewing a detected image screen captured by the endoscope tube 2 after the endoscope host 1 is turned on, the main body 10 further includes a display device 15 telecommunicatively connected to the processing unit 14 for displaying the image captured by the endoscope tube 2.

In addition, the organ identification unit 13 further includes an organ tube identification mode and stores an organ tube comparison table, and the organ tube identification unit 13 compares the received type signal with the organ tube comparison table to determine the corresponding organ tube type of the endoscope tube 2 and output an examined image signal accordingly. The processing unit 14 stores a plurality of endoscopic imaging modes, so that after the examined image signal is received, the corresponding endoscopic imaging mode is executed, and the image captured by the endoscope tube is displayed. Wherein, the organ tube identification mode at least can detect two or more selected from the group consisting of the large intestine probe (1111), duodenum probe (1101), colon probe (1110), sigmoid colon probe (1011), bronchus probe (1010), small intestine probe (1001), ureter probe (1000), bladder probe (0111), nose probe (0101), throat probe (0100), esophagus probe (0011), gallbladder probe (0010), stomach probe (0001), and joint probe (0000). The numbers in parentheses above represent the random coded data of the corresponding organs in the organ comparison table. In the organ tube identification mode, after the endoscope host 1 is inserted with the endoscope tube 2 of any type, the endoscope tube 2 can be directly used to perform the examination operation to the corresponding organ of the examinee, thereby not just can tell the type of the endoscope tube 2 only, but also can achieve the "one host applicable for various different types of endoscopic tubes" effect. Wherein, the execution of the organ tube identification mode can identify the organ as described above while generating the result image simultaneously. In other words, users can switch the operation, such that after the endoscope tube 2 is inserted from the connecting hole 102 of the endoscope host 1 and electrically conducted with the electrical connection driving part 11 and the electrical connection identification part 12, the organ identification unit 13 just compares the type signal with the organ comparison table or just compare the type signal with the organ tube comparison table, or the organ identification unit 13 simultaneously compares the type signal with the organ comparison table and the organ tube comparison table. As a result, the endoscope host 1 can determine the organ type of the endoscope tube 2 and match the organ type directly with each for a direct application.

Preferably, the plurality of endoscopic imaging modes includes gastroscopic imaging mode, duodenoscopic imaging mode, colonoscopic imaging mode, sigmoidoscopic imaging mode, colonoscopic imaging mode, bronchoscopic imaging mode, ureteroscopic imaging mode, cystoscopeic imaging mode, rhinolaryngoscopic imaging mode, thoracoscopic imaging mode, laryngoscopic imaging mode, choledochoscopic imaging mode, arthroscopic imaging mode, colposcopic imaging mode, enteroscopic imaging mode, otoscopic imaging mode, laparoscopic imaging mode, etc. so that the endoscope host 1 can be applicable for most common endoscopic examination types, and drive and used by various different types of endoscope tubes 2.

More specifically, a preferred setting can be set to drive the organ identification unit 13 corresponding to the endoscope tube with a corresponding organ tube type to store an image clarity parameter, wherein when the endoscope tube is applied for joint examination, the image clarity parameter falls within a range of 5~35 mm; when the endoscope tube is applied for stomach examination, the image clarity parameter falls within a range of 5~100 mm; when the endoscope tube is applied for vaginal examination, the image clarity parameter falls within a range of 15~50 mm; when the endoscope tube is applied for bronchial and bladder examination, the image clarity parameter falls within a range of 3~50 mm; when the endoscope tube is applied for colon examination, the image clarity parameter falls within a range of 2~100 mm; when the endoscope tube is applied for abdominal cavity examination, the image clarity parameter falls within a range of 15~120 mm; and when the endoscope tube is applied for duodenal examination, the image clarity parameter falls within a range of 4~90 mm. In this way, after the endoscope tube 2 of any type is inserted into the main body 10, the organ identification unit 13 can determine the corresponding organ, while setting up the image clarity parameter according to the imaging requirement of the organ detection, so that when the endoscope tube 2 performs an examination operation through the endoscope host 1, adjustments can be made according to the aforementioned parameter range in order to obtain a clear image captured by the endoscope tube 2. In addition, the organ identification unit 13 further stores a micro-imaging parameter preferably falling within a range of 1~5 mm. To reiterate, misidentification can be prevented effectively by means of the signal path identification confirmation key 122. When the identification accuracy is improved, adjustments to a wrong image clarity parameter that make the detected image too blurry and too difficult to diagnose the symptoms, and lead to delayed treatment, wrong examination and even bad situation such as excision of organs or limbs can be prevented.

Figure 4:
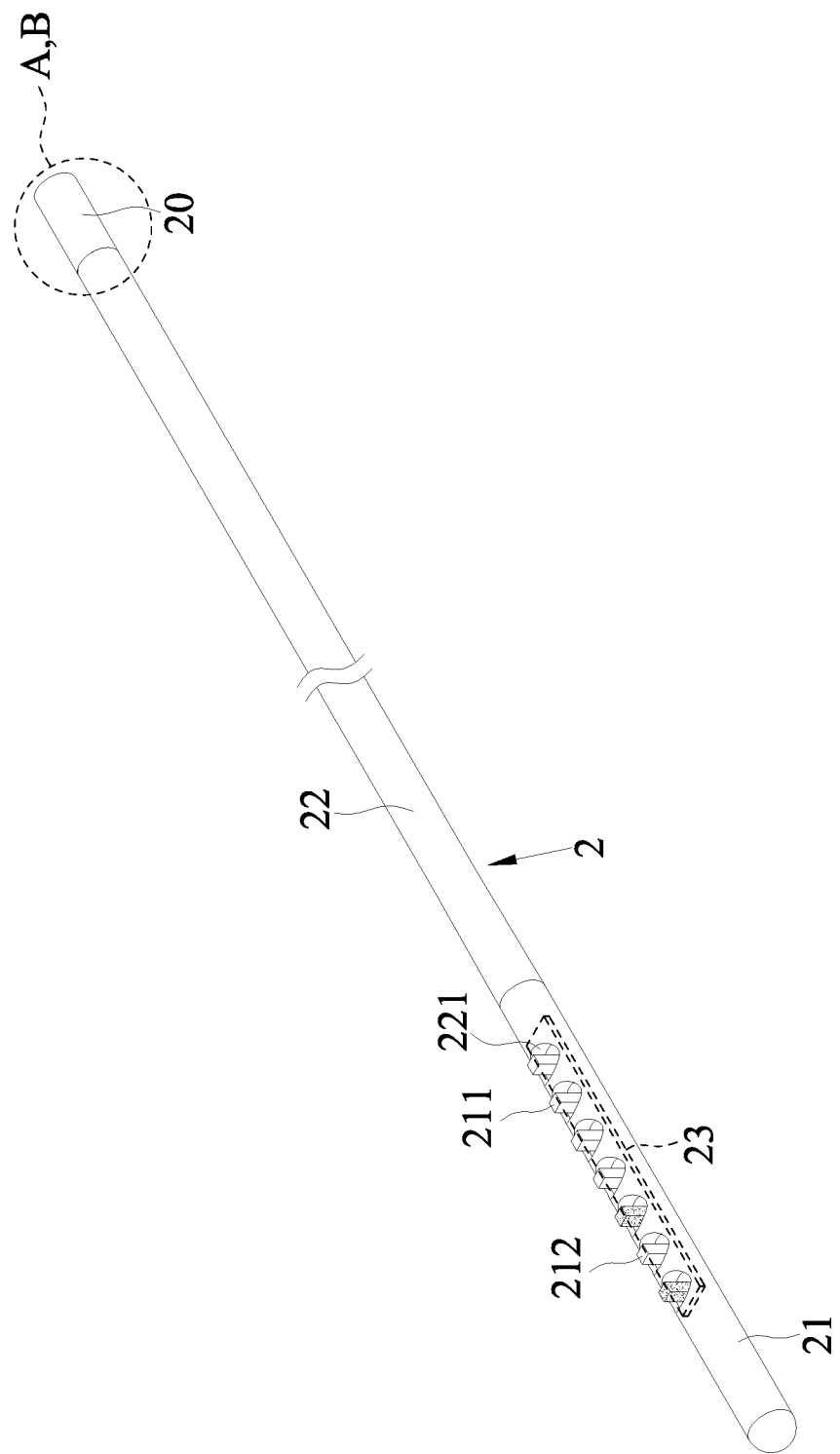
FIG. 4 is a perspective view of an endoscope tube of a preferred embodiment of this disclosure.
Figure 5:
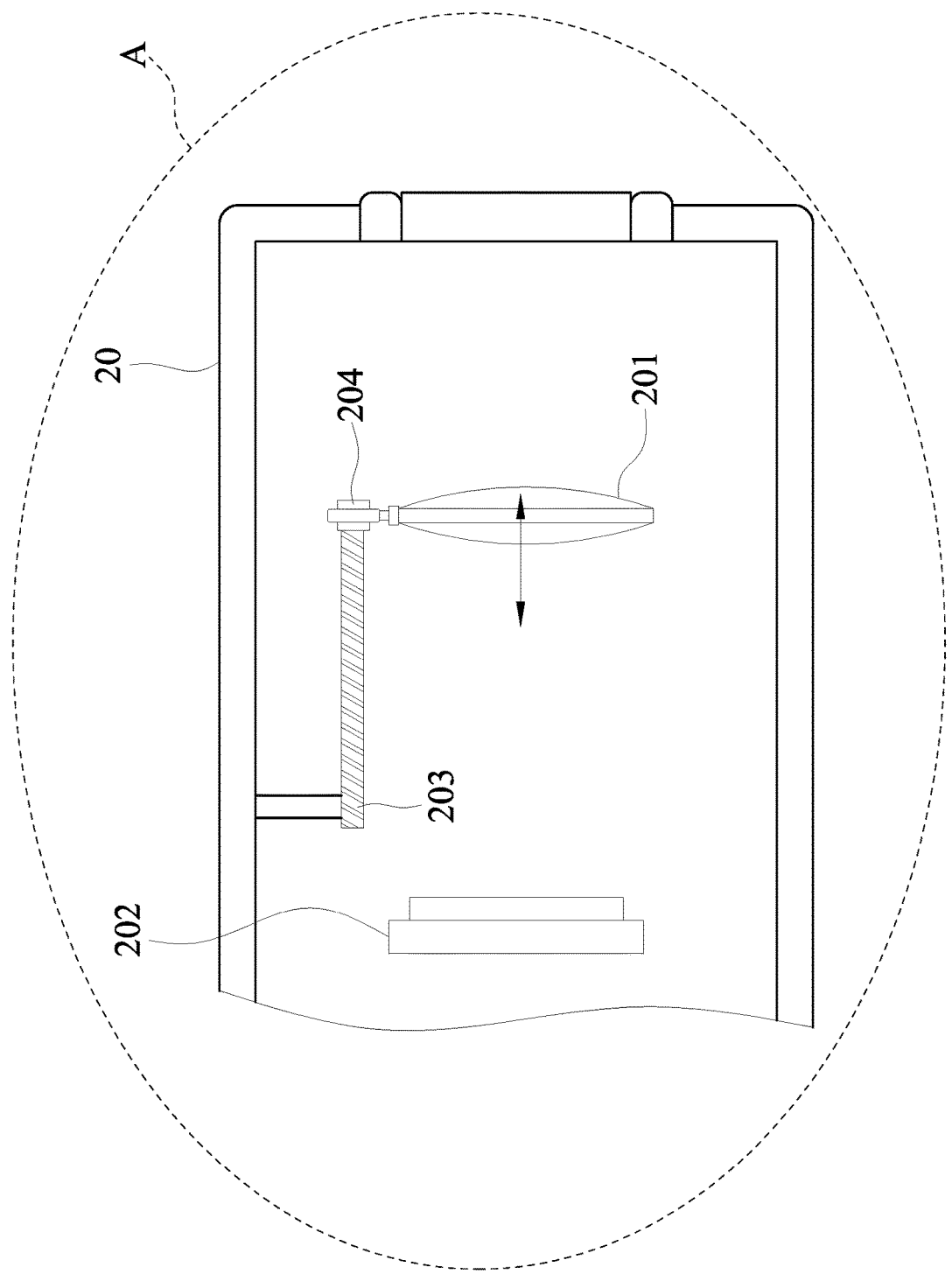
FIG. 5 is a partial schematic view of an endoscope tube of a preferred embodiment of this disclosure.
Figure 6:
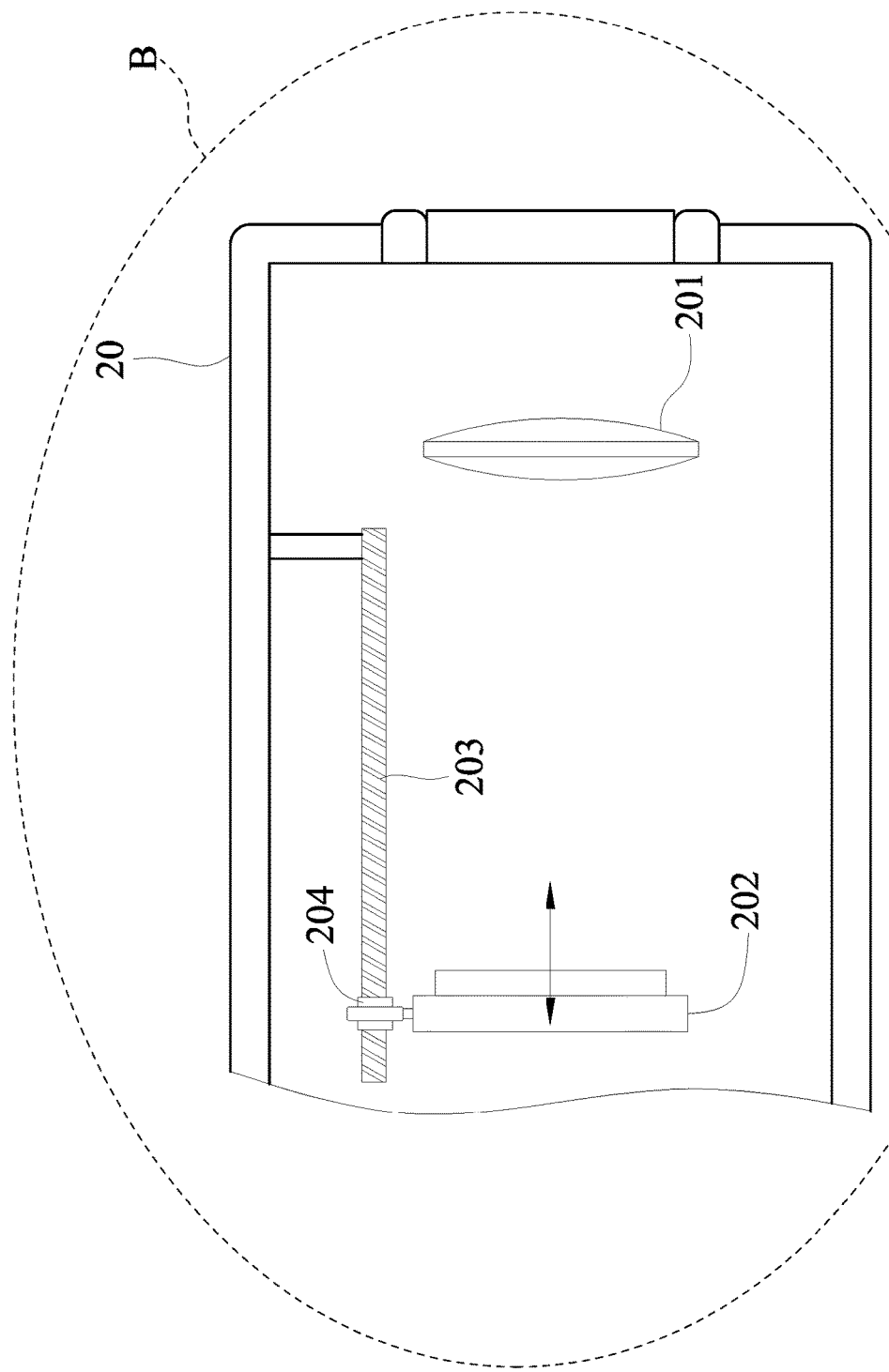
FIG. 6 is a partial schematic view of an endoscope tube in accordance with another implementation mode of a preferred embodiment of this disclosure.
Figure 7:
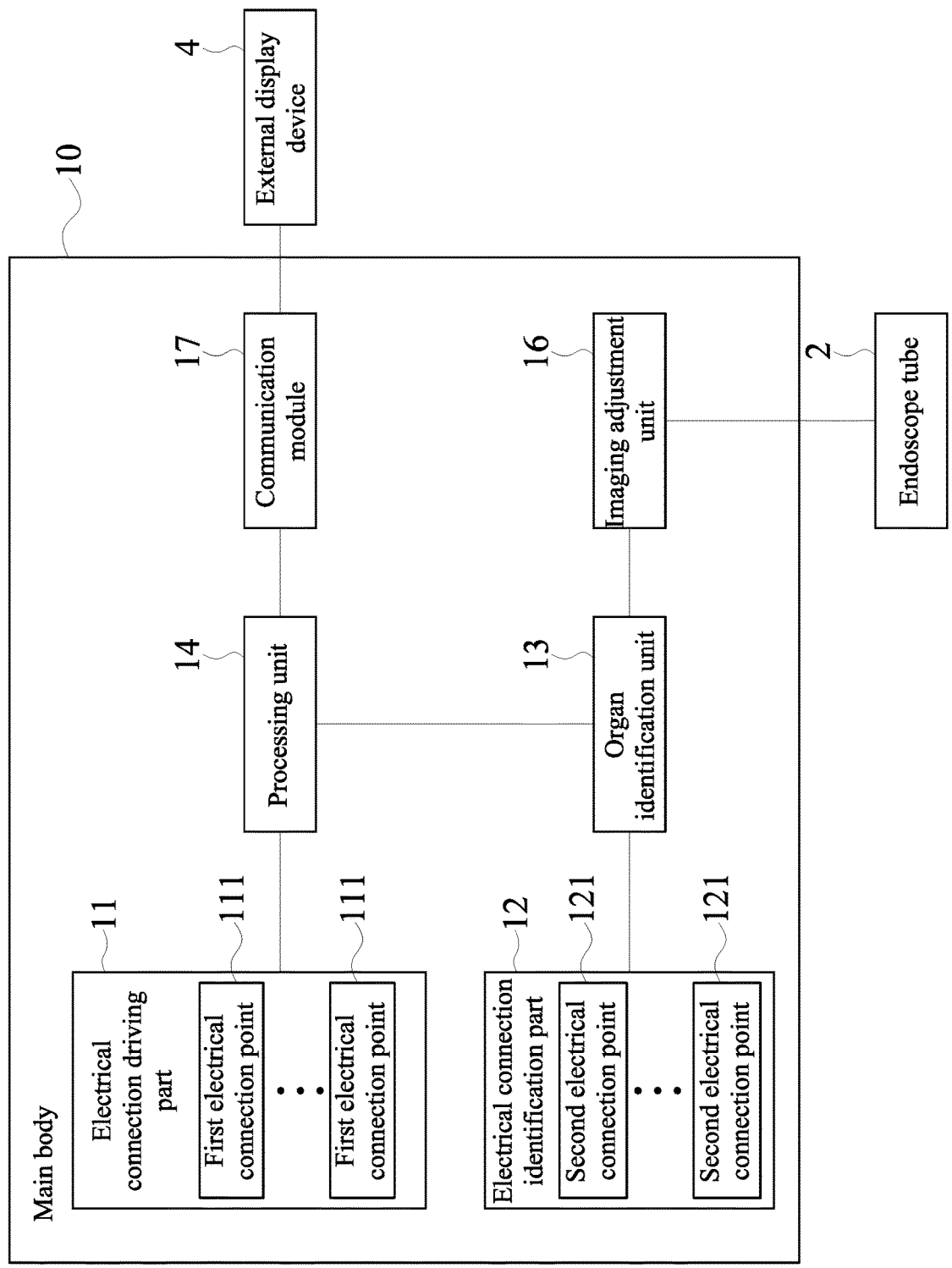
FIG. 7 is another schematic block diagram of a preferred embodiment of this disclosure.

With reference to FIGS. 4 to 7, FIGS. 5 and 6 are blow-up views of the internal structures of a shooting end 20 of the endoscope tube 2 as shown in FIG. 4, the main body 10 further includes an imaging adjustment unit 16 telecommunicatively connected to the endoscope tube 2 and the organ identification unit 13, and provided for adjusting the distance between a lens 201 of a endoscope tube 2 and an imaging sensing element 202 by linearly displacing either one of the lens 201 and the imaging sensing element 202 according to the image clarity parameter and/or the micro-imaging parameter in order to produce a clear image, wherein the endoscope tube 2 further includes a screw 203 and a corresponding thread element 204, and the corresponding thread element 204 is installed into a thread groove formed on the screw 203 and connected to the lens 201, such that the imaging adjustment unit 16 can drive and rotate the screw 203 for example, via a wireless transmission, to move the lens 201 forward, or away from the imaging sensing element 202 as shown in FIG. 5, or the corresponding thread element 204 is connected to the imaging sensing element 202, such that the imaging adjustment unit 16 can rotate the screw 203 to move the imaging sensing element 202 forward or away from the lens 201 as shown in FIG. 6. In this way, the endoscope tubes 2 of different types can capture clearer images. For example, when the endoscope tube 2 is applied for joint examination, since a joint opening is smaller than 50 mm, the image clarity parameter falls within a range of 5~35 mm; when the endoscope tube 2 is applied for stomach examination, since the diameter of stomach is smaller than 250 mm, the image clarity parameter falls within a range of 5~100 mm; when the endoscope tube 2 is applied for vaginal examination, the diameter of vagina is smaller than 35 mm, the image clarity parameter falls within a range of 15~50 mm; when the endoscope tube 2 is applied for bronchus or bladder examination, since the diameter of bronchus is smaller than 30 mm, and the diameter bladder is smaller than 100 mm, the image clarity parameter falls within a range of 3~50 mm; when the endoscope tube 2 is applied for colon examination, since the diameter of colon is smaller than 50 mm, the image clarity parameter falls within a range of 2~100 mm; when the endoscope tube 2 is applied for abdominal cavity examination, since the diameter of abdominal cavity is smaller than 600 mm, the image clarity parameter falls within a range of 15~120 mm; and when the endoscope tube 2 is applied for duodenum examination, since the diameter of duodenum is smaller than 40 mm, the image clarity parameter falls within a range of 4~90 mm.

Figure 8:
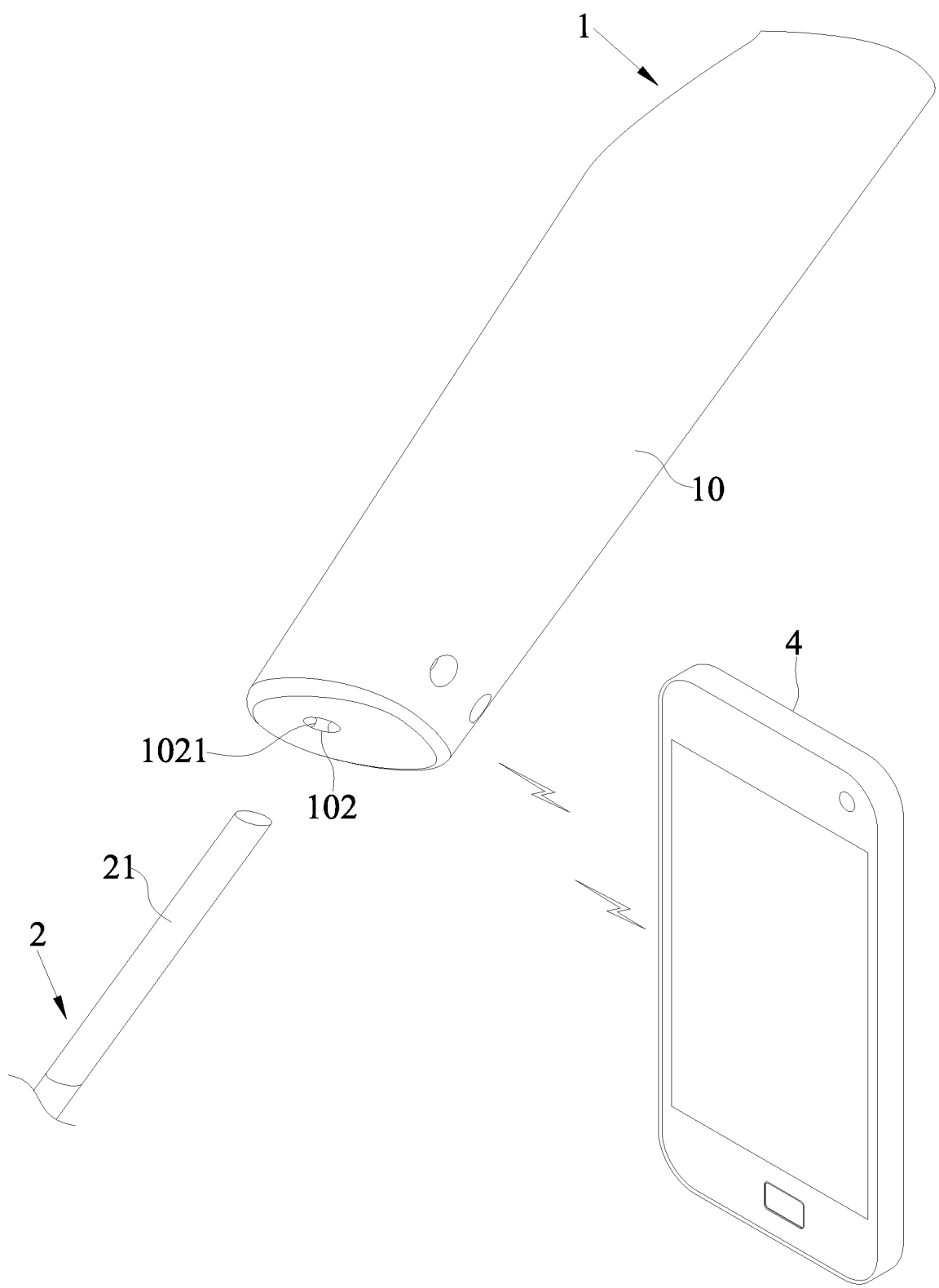
FIG. 8 is a schematic view of another application of a preferred embodiment of this disclosure.

With reference to FIG. 8, the image captured by the endoscope tube 2 is directly displayed at the main body 10, and the main body 10 can have a communication module 17 telecommunicatively connected to an external display device 4 and the processing unit 14 for displaying the image captured by the endoscope tube 2 through the external display device 4 to achieve the remote viewing effect. In addition, the endoscope tubes 2 of various different diameters can be put into the connection channel 101 from the connecting hole 102 successfully, and the connecting hole 102 contains at least one elastic member 1021 for elastically pressing the endoscope tube 2 when the endoscope tube 2 is inserted into the connection channel 101, so that the endoscope host 1 can be securely assembled with the endoscope tubes 2 of different diameters. Wherein, the organ identification unit 13 of the main body 10 of this embodiment also includes the organ comparison table and the organ tube comparison table, but the type of the organ comparison table and the organ tube comparison table has be shown in FIG. 3, so that the communication module 17 and the external display device 4 are not shown in the figure for the illustration. Please refer to FIG. 3 for the contents of the preferred type of the organ comparison table and the organ tube comparison table.

With reference to FIGS. 1 to 8 for an endoscope device for intelligently detecting organs 3 in accordance with this disclosure, the endoscope device includes the endoscope host 1 and an endoscope tube 2, and the endoscope tube 2 has a shooting end 20 and a connecting end 21, and the connecting end 21 has a plurality of third electrical connection points 211 and at least one fourth electrical connection point 212, which are arranged in a linearly vertical manner, and when the connecting end 21 of the endoscope tube 2 is inserted into the connecting hole 102, the plurality of third electrical connection points 211 is electrically conducted with the plurality of first electrical connection points 111, and the fourth electrical connection point 212 is electrically conducted with the second electrical connection point 121, wherein, the fourth electrical connection point 212 refers to the conductive structure electrically conducted with the second electrical connection point 121, and the endoscope tube 2 can directly have one or more fourth electrical connection points 212 with the electrically conductive property or the endoscope tube 2 can have a plurality of contact structures, but the fourth electrical connection point 212 as described here is only a contact with an electrically conductive property. The endoscope tube 2 can be electrically conducted with a part or all of the second electrical connection points 121 depending on the quantity of the fourth electrical connection points 212 on the endoscope tube 2. In order to facilitate inserting the endoscope tube 2 into the main body 10 smoothly, the plurality of second electrical connection points 121 and the plurality of first electrical connection points 111 in the main body 10 of the endoscope host 1 are preferably arranged in a linearly vertical manner, so that the endoscope tube 2 can be plugged and unplugged vertically in an application, so as to make the use more easily.

Figure 1B:
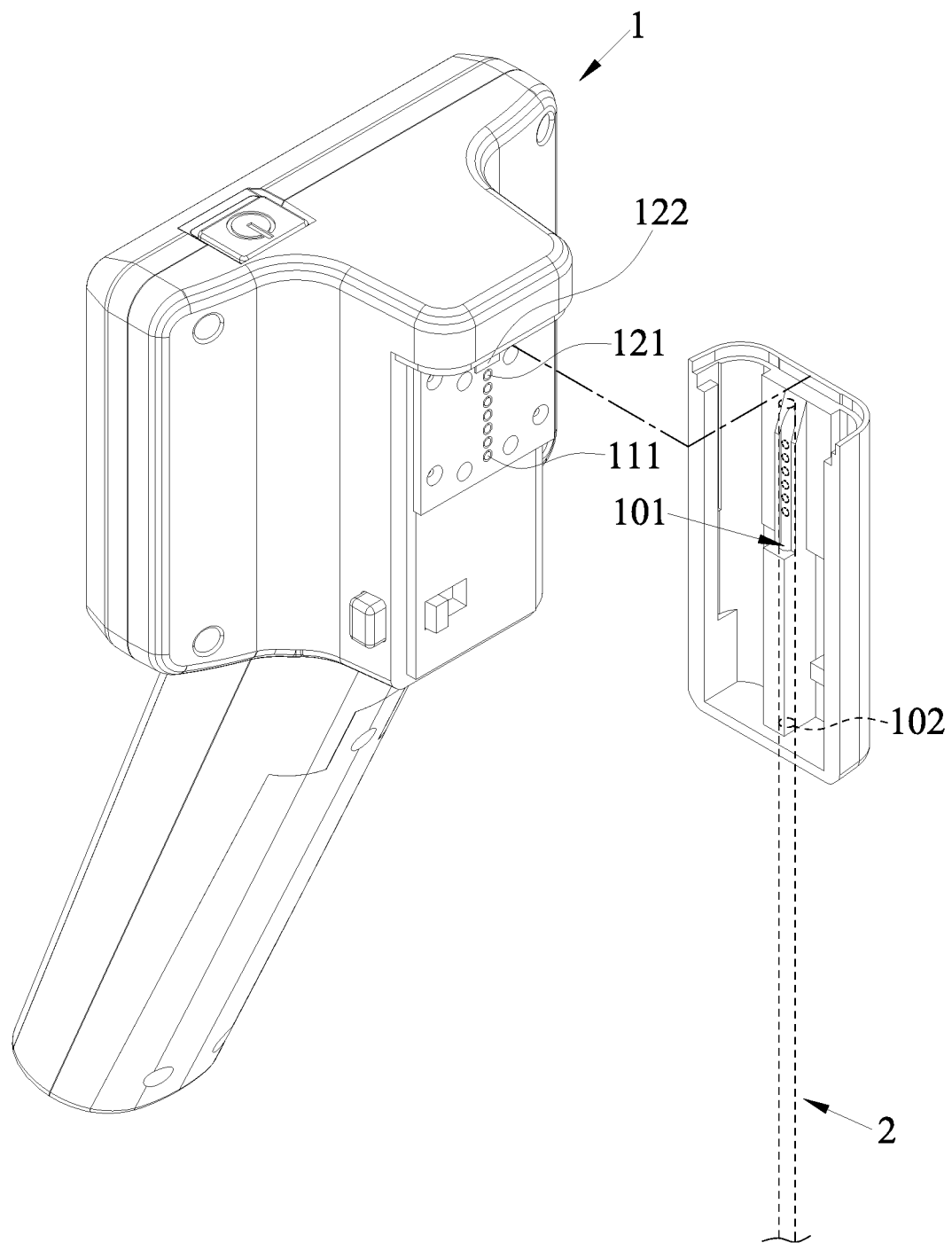
FIG. 1B is a partial exploded view of an endoscope host and an endoscope tube in accordance with a preferred embodiment of this disclosure.
Figure 1C:
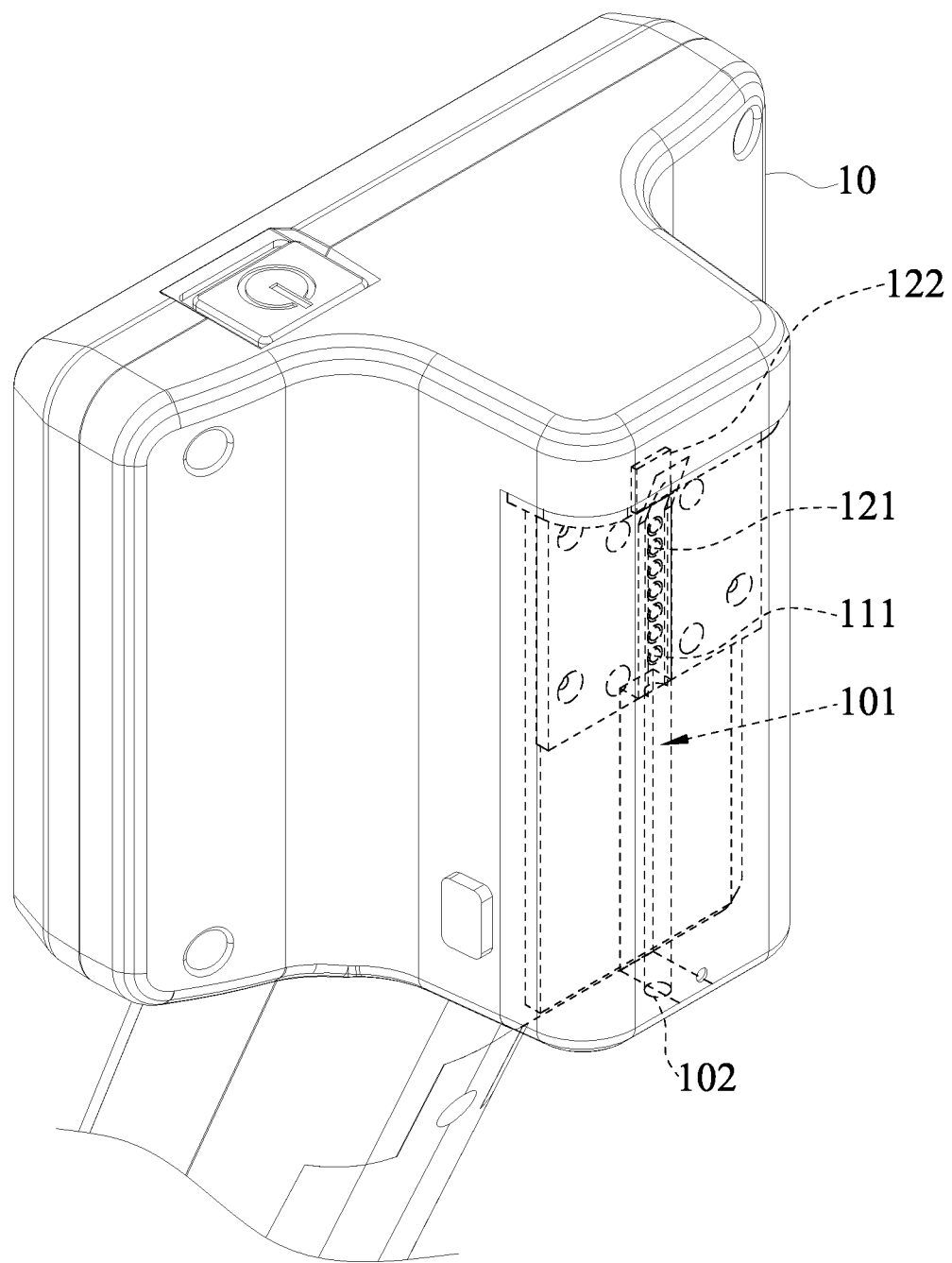
FIG. 1C is a first partial perspective view of an endoscope host in accordance with a preferred embodiment of this disclosure.

The plurality of third electrical connection points 211 and the fourth electrical connection points 212 can be electrically conducted with the plurality of first electrical connection points 111 and the second electrical connection points 121 of the endoscope host 1 to generate the execution signal and the type signal, so that the endoscope host 1 can automatically determine the application type of the endoscope tube 2 and execute the corresponding endoscopic imaging mode to facilitate users to start performing an endoscopic test, improve the convenience of the endoscopic test and relatively lower the machine cost. Wherein, the shooting end 20 has the lens 201, the imaging sensing element 202, the screw 203, the corresponding thread element 204 and at least one light emitting element (not shown in the figure) provided for capturing an image of a detected part. In this embodiment, the connecting end 21 of the endoscope tube 2 has a plurality of contacts, but only a part of the contacts such as the fourth electrical connection points 212 (which are indicated in the area of FIG. 4) have the electrically conductive property. In the actual product of the endoscope device 3, one endoscope host 1 is equipped with one endoscope tube 2 or a plurality of endoscope tubes 2 with different designs of the fourth electric contacts 212 to form a combined testing device applicable for various different detection positions as shown in FIGS. 1A to 1C.

Figure 2A:
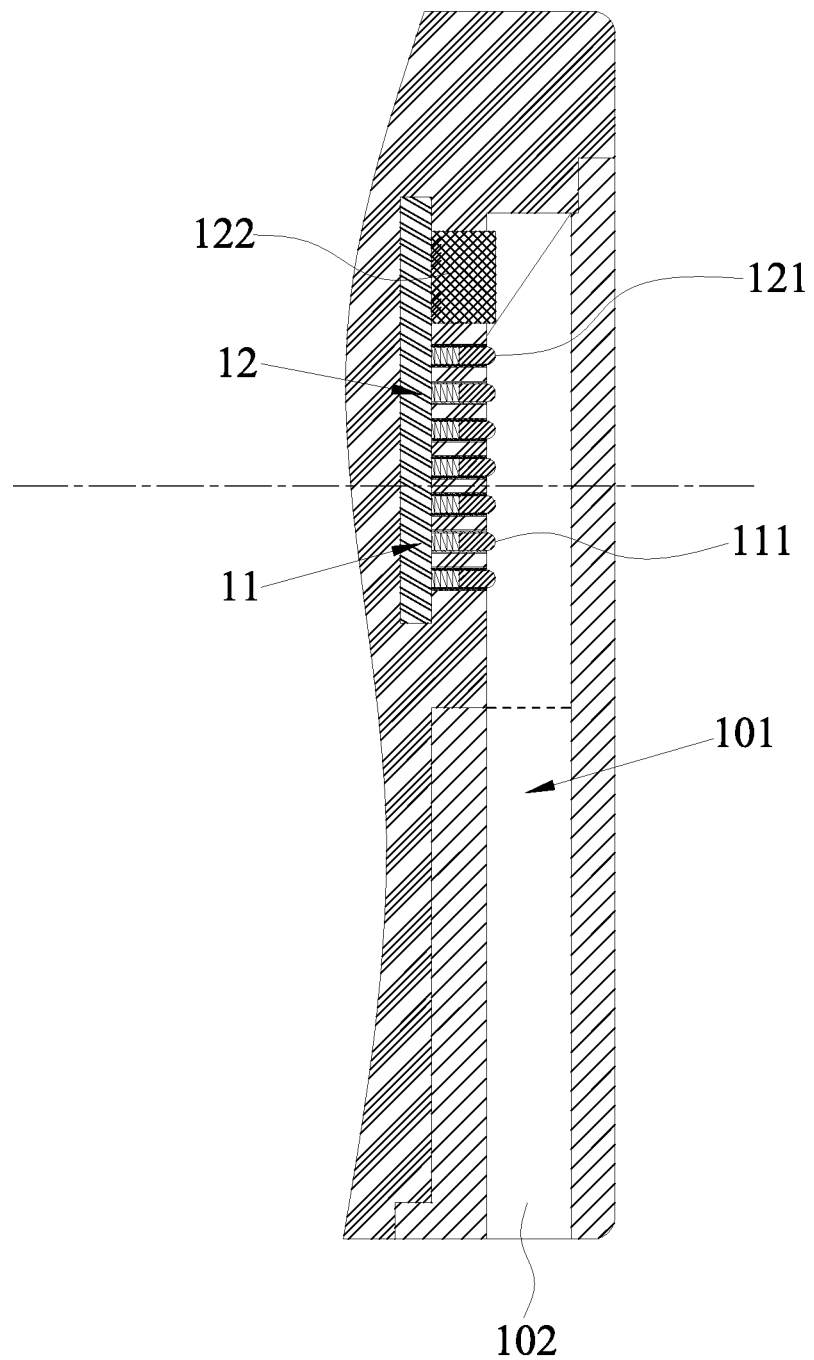
FIG. 2A is a partial schematic view of an endoscope host in accordance with a preferred embodiment of this disclosure.
Figure 2B:
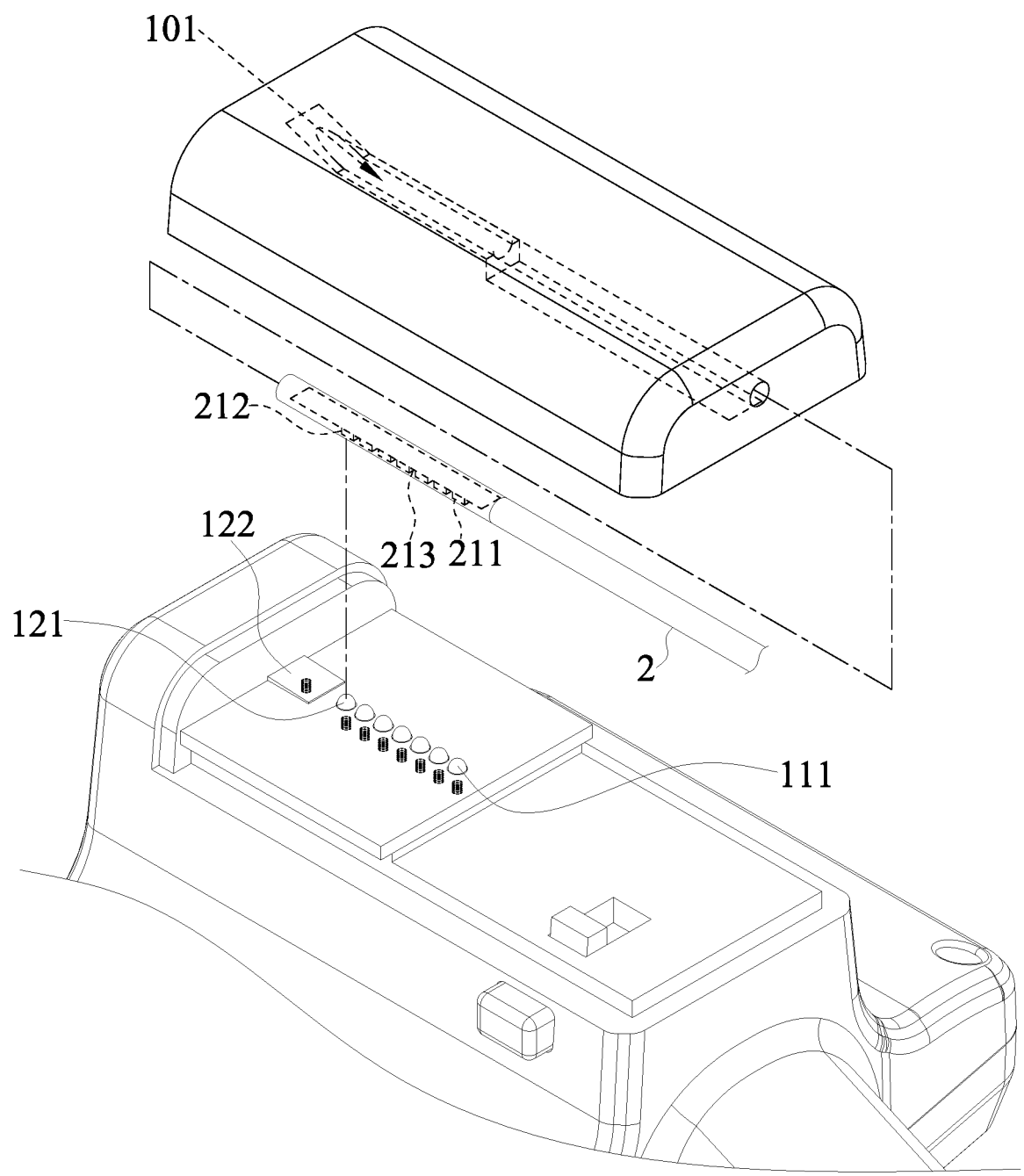
FIG. 2B is a partial schematic perspective view of an endoscope host and an endoscope tube in accordance with a preferred embodiment of this disclosure.
Figure 2C:
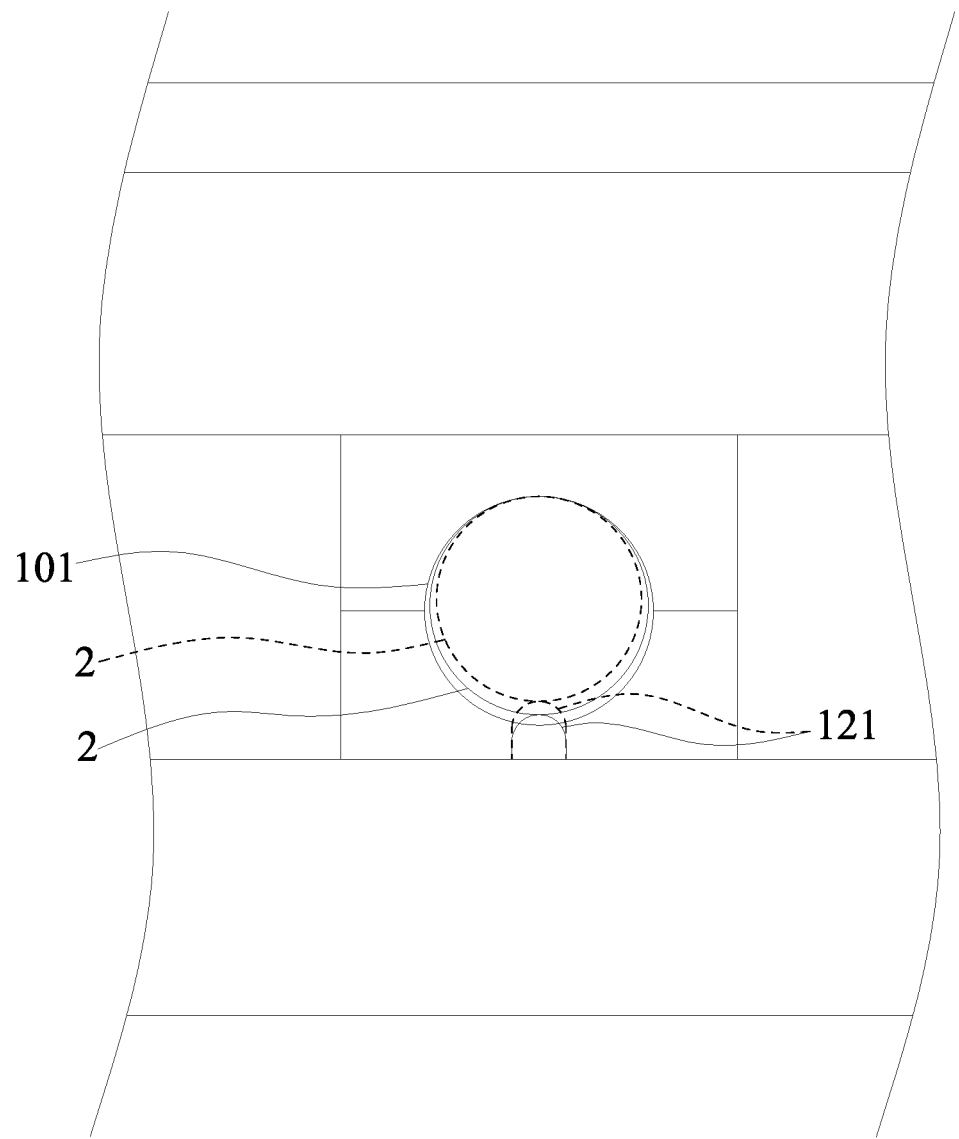
FIG. 2C is a schematic view showing an application of an endoscope host installed with an endoscope tube of different diameter in accordance with a preferred embodiment of this disclosure.
Figure 3:
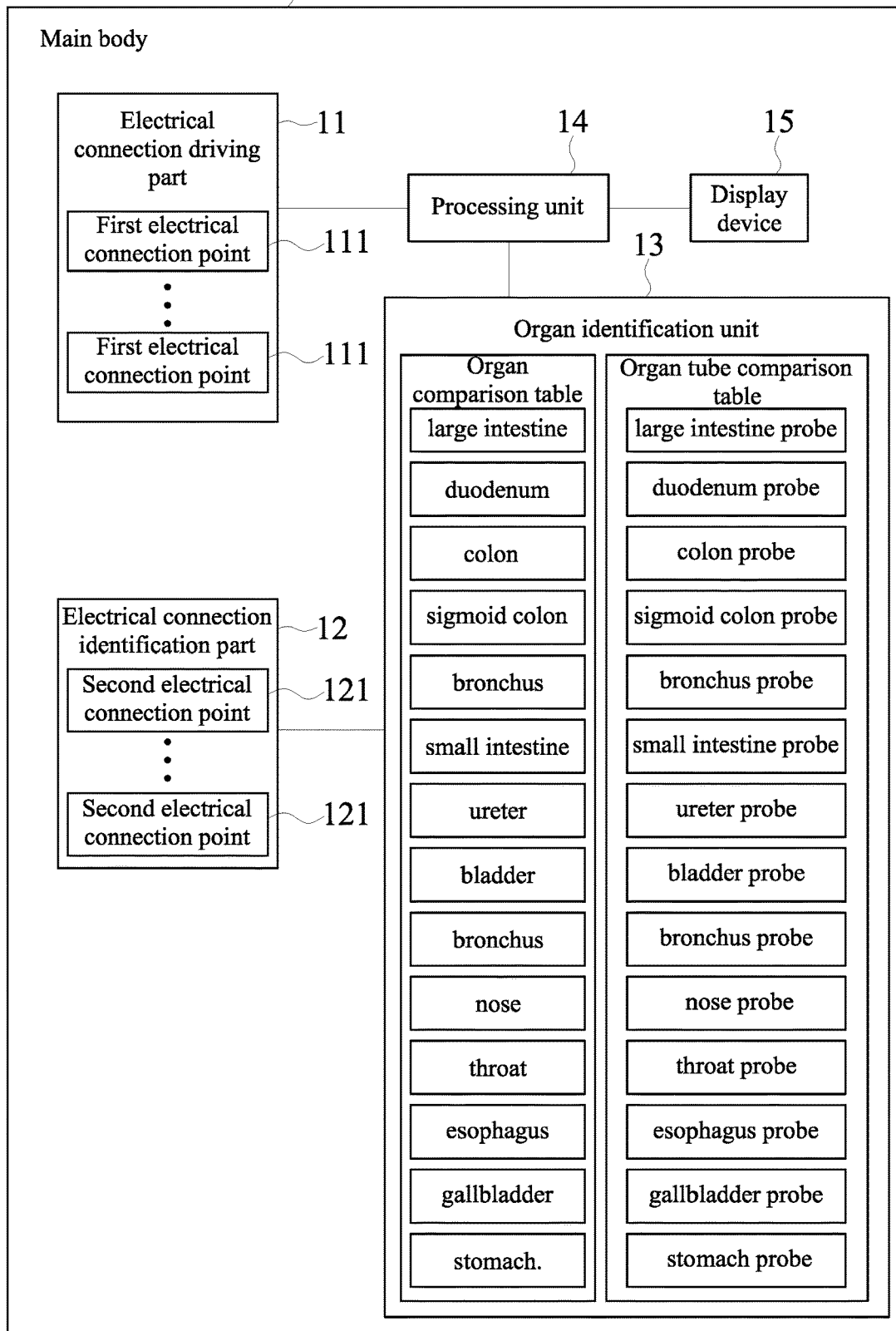
FIG. 3 is a schematic block diagram of a preferred embodiment of this disclosure.

Preferably, the endoscope tube 2 is designed as shown in FIG. 2B, wherein the plurality of third electrical connection points 211 and the plurality of fourth electrical connection points 212 are arranged with an internal apart and in a protruding form, and a depression 213 is formed between any two adjacent third electrical connection points 211 and fourth electrical connection points 212, and the plurality of third electrical connection points 211 and the plurality of fourth electrical connection points 212 have a surface roughness smaller than the surface roughness of the depression 213. After the endoscope tube 2 and the endoscope host 1 are assembled with each other, the plurality of third electrical connection points 211 and the plurality of fourth electrical connection points 212 can touch the plurality of first electrical connection points 111 and the plurality of second electrical connection points 121 more easily and securely, while the design of the large surface roughness of the plurality of depressions 213, the endoscope tube 2 will not slide easily after it is put into the connection channel 101, so that the plurality of third electrical connection points 211 and the plurality of fourth electrical connection points 212 keeps touching the plurality of first electrical connection points 111 and the plurality of second electrical connection points 121 to facilitate the endoscope host 1 to make a determination.

In FIG. 4, the endoscope tube 2 includes a casing 22 and a circuit board 23, and the plurality of third electrical connection points 211 and the fourth electrical connection point 212 are installed on the circuit board 23, and the casing 22 is sheathed on an outer side of the circuit board 23 and has a plurality of holes 221, and the plurality of third electrical connection points 211 and the fourth electrical connection point 212 are exposed. Wherein, the circuit board 23 is a flexible printed circuit board, and the casing 22 is made of a flexible material, to improve the convenience of using the endoscope tube 2. In addition, the endoscope tube 2 has a maximum diameter falling within a range of 0.5~14 mm, which can be changed within the range according to the testing human parts. For example, the endoscope tube applied for stomach examination has a diameter falling within a range of 9~11.4 mm; the endoscope tube applied for duodenal examination has a diameter falling within a range of 10.8~12.5 mm; the endoscope tube applied for Colon examination has a diameter falling within a range of 12.9~13.7 mm; the endoscope tube applied for sigmoid colon examination has a diameter falling within a range of 12.8~13.2 mm; the endoscope tube applied for intestinal examination has a diameter falling within a range of 10.5~11.7 mm; the endoscope tube applied for bronchial examination has a diameter falling within a range of 5.7~6 mm; the endoscope tube applied for ureteral examination has a diameter falling within a range of 2.8~3.3 mm; the endoscope tube applied for bladder examination has a diameter falling within a range of 5.4~5.5 mm; the endoscope tube applied for nose and throat examination has a diameter falling within a range of 2~5 mm; the endoscope tube applied for biliary tract examination has a diameter falling within a range of 2.8~5.2 mm; the endoscope tube applied for chest examination has a diameter of 7 mm; and the endoscope tube applied for intubated throat examination has a diameter falling within a range of 4.1~5.2 mm.

Figure 9:
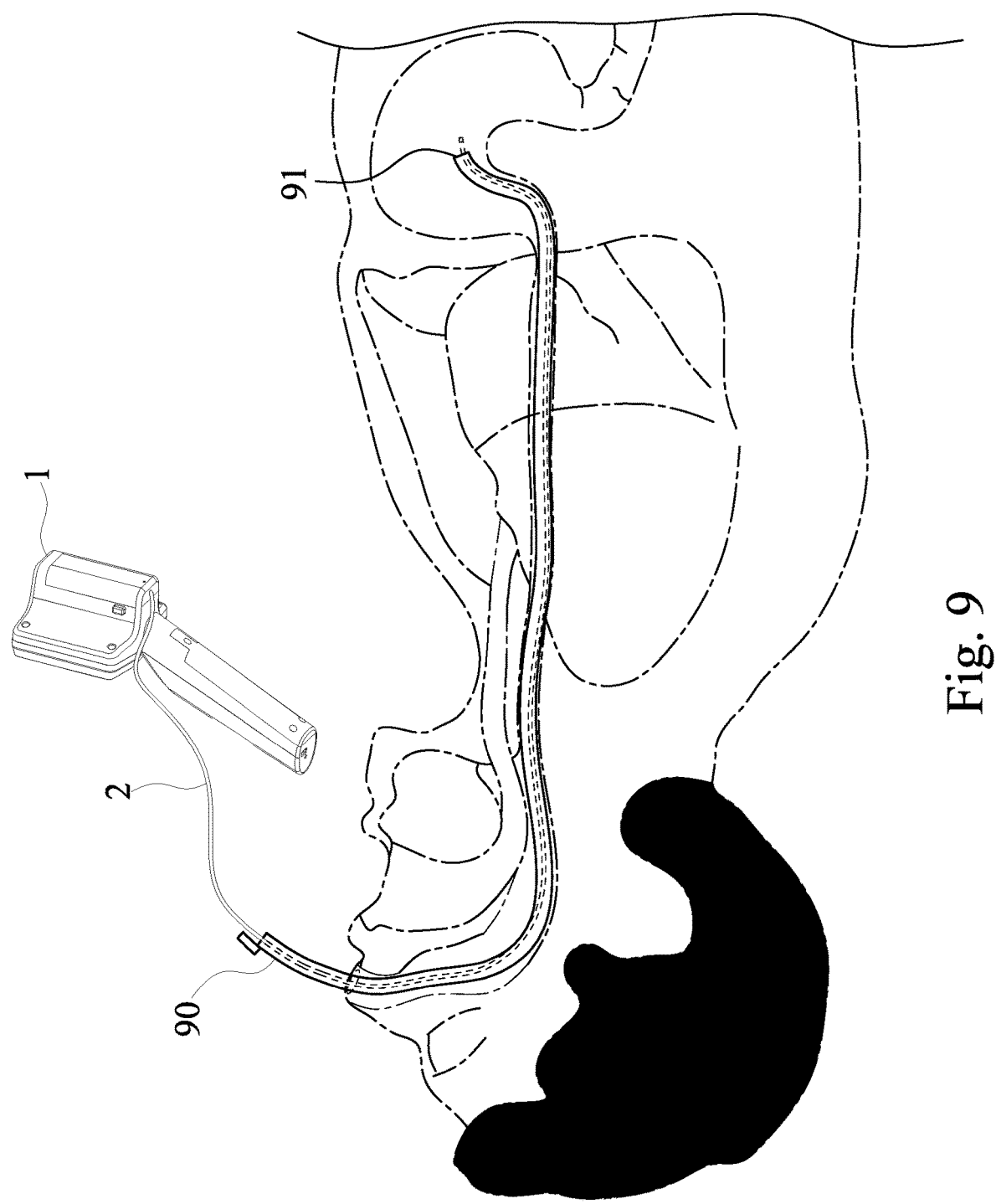
FIG. 9 is a first schematic view showing an application of a preferred embodiment of this disclosure used for changing a nasogastric tube.
Figure 10:
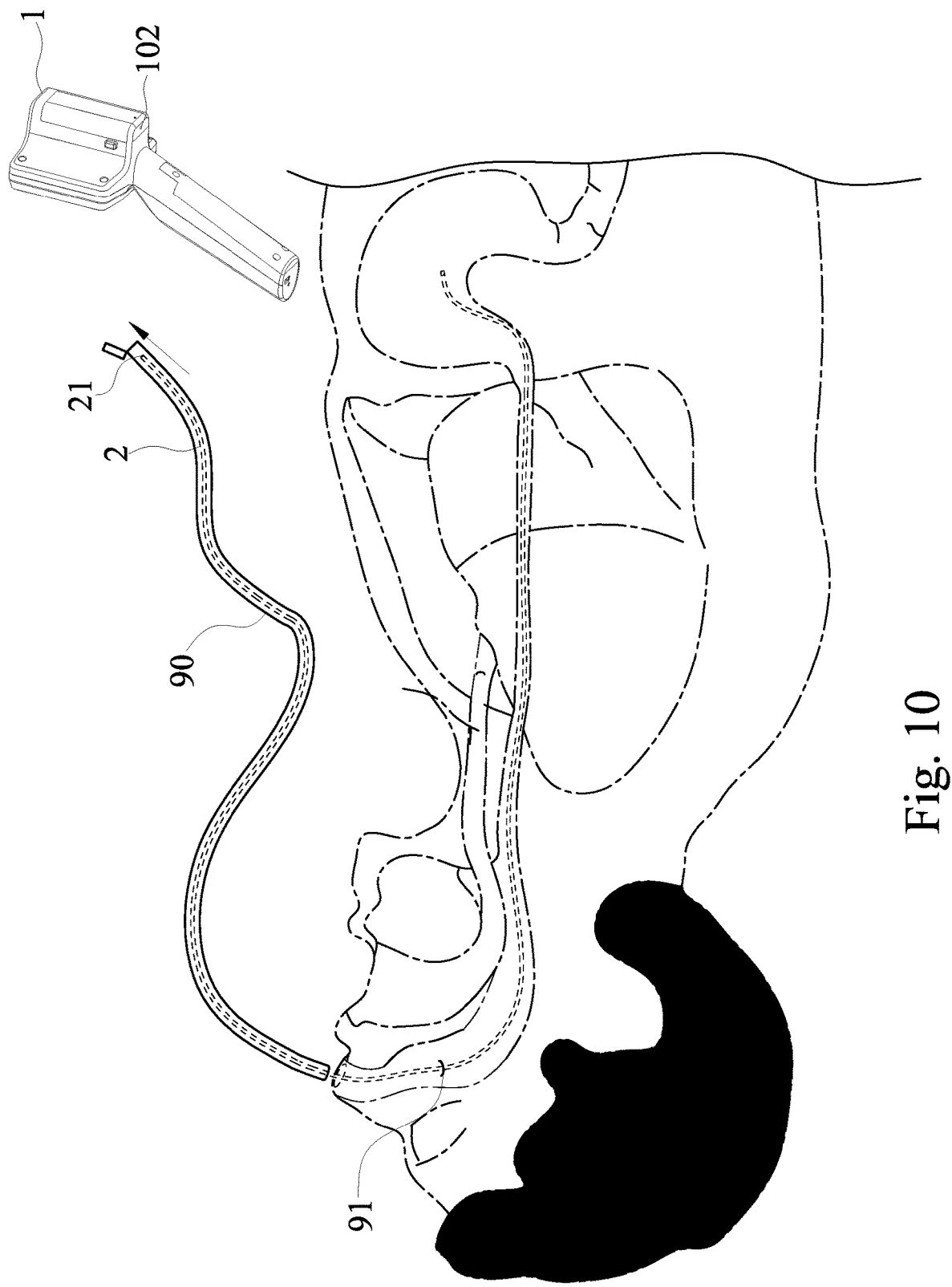
FIG. 10 is a second schematic view showing an application of a preferred embodiment of this disclosure used for changing a nasogastric tube.
Figure 11:
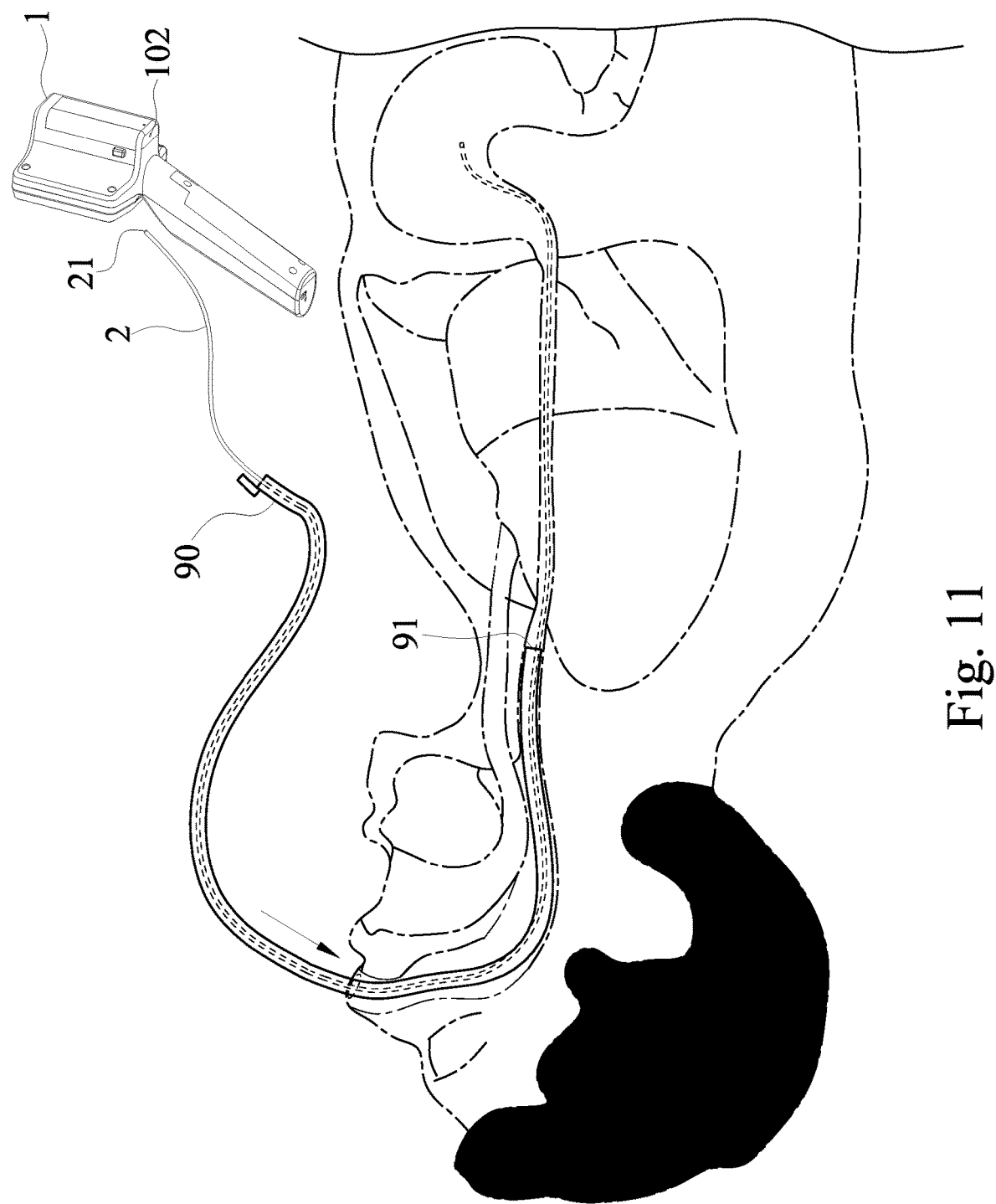
FIG. 11 is a third schematic view showing an application of a preferred embodiment of this disclosure used for changing a nasogastric tube.

With reference to FIGS. 9 to 11 for the first to third schematic views of the application in accordance with a preferred embodiment of this disclosure respectively, the endoscope tube 2 can be used for an image examination of different organs of a human body and can also be used as an aid for changing the nasogastric tube, and the present commonly used nasogastric tube has a diameter approximately falling within a range of 2 mm~5.5 m. When the diameter of the endoscope tube 2 falls within a range of 2~5 mm, the endoscope tube 2 can be designed with a hardness falling within a range of Shore 50~80 A. In this way, the endoscope tube 2 can be used for nose and throat examination, and the endoscope tube 2 can also be used for guiding the change of the nasogastric tube. After the endoscope tube 2 is put into the nasogastric tube from the exposed end 90 of the human nasogastric tube and extended to an end 91 of a human stomach, the nasogastric tube is withdrawn along the endoscope tube 2, and then another nasogastric tube is sheathed on the connecting end 21 of the endoscope tube 2, and the nasogastric tube is inserted into the human body along the endoscope tube 2 for positioning. The endoscope tube concurrently has an examination effect as well as an effect of guiding the nasogastric tube, so that the hardness of the endoscope tube 2 can be limited within a range of Shore 50~80 A to facilitate extending the endoscope tube 2 into the human body, while it will not be too soft that causes the nasogastric tube to be difficult to move along the endoscope tube 2. Of course, when the endoscope tube 2 is intended to be applied for changing the nasogastric tube, the aforementioned diameter range of the endoscope tube 2 can be chosen according to the diameter of the nasogastric tube.

In FIG. 9, when the nasogastric tube has been put into the human body, the endoscope tube 2 can be entered into the nasogastric tube from the exposed end 90 of the nasogastric tube and then moved along the nasogastric tube into the stomach. At this time, the endoscope tube 2 and the endoscope host 1 can maintain the electrical connection status. Since the nasogastric tube is made of a transparent material, therefore the endoscope tube 2 still can observe the status of the nose, esophagus and stomach. When it is necessary to change the nasogastric tube, the connecting end 21 of the endoscope tube 2 is removed from the connecting hole 102, such that the nasogastric tube placed in the human body can be withdrawn along the endoscope tube 2 as shown in FIG. 10. After the original nasogastric tube is removed, a new nasogastric tube can be sheathed on an endoscope tube 2 from the connecting end 21, and the nasogastric tube in inserted into the human body along the endoscope tube 2 for positioning, so as to complete changing the nasogastric tube. After the nasogastric tube is inserted to a required length, the connecting end 21 of the endoscope tube 2 can be inserted into the connecting hole 102 again to continue performing the image capture examination, and confirm the status of the nasogastric tube, and then the endoscope tube 2 is moved slowly away from the human body to assist the operating of placing the nasogastric tube. When the plurality of first electrical connection points 111, the plurality of second electrical connection points 121, the plurality of third electrical connection points 211 and the fourth electrical connection point 212 are arranged in a linear configuration, the nasogastric tube can be sheathed on the endoscope tube 2 and slid to the nasal cavity, the esophagus and the stomach more easily.

In practice, when a new nasogastric tube is placed, there is a certain chance of misplacing the nasogastric tube. For example, after the nasogastric tube enters the nose and extends to the trachea instead of the esophagus, a fatal and severe risk will be imposed on a patient if the aforementioned situation has not been discovered and the patient eats foods thereafter. Therefore, in the past, it was necessary to take a chest X-ray to confirm the correct position of the nasogastric tube placed into the patient's body. However, this method requires an additional inspection process, and most of the time, the patient needs to go to the X-ray laboratory before the inspection can be completed, thereby resulting in extreme inconvenience. In view of this problem, this discloser conceives an idea of allowing the endoscope tube 2 to have an examination effect and serve as a guide tool of placing the nasogastric tube to improve the accuracy, safety and speed of the nasogastric tube during its placement without the need of confirming the position of the nasogastric tube by X-ray after the placement.

In summation of the description above, the endoscope host 1 and the endoscope device 3 as disclosed in this disclosure use the electrical conduction status to detect what endoscope type corresponding to the inserted endoscope tube 2, so as to achieve the effect of "knowing what organ is detected upon the insertion of the inserted endoscope tube" and can further automatically switch to the corresponding imaging mode to facilitate the control, operation and use of the endoscope device by the examiner, and this disclosure has an excellent "one host for various different endoscope tubes" effect. From the designer's point of view, it no longer needs to develop and design new electrical structures of endoscope tubes with various different specifications one by one for the endoscope host. From the user's point of view, the machine cost can be lowered significantly.

What is claimed is:

1. An endoscope host for intelligently detecting organs, comprising:
    a main body, having a connection channel, a connecting hole formed on an external surface of the main body, and the connection channel and the connecting hole communicating to each other and provided for inserting an endoscope tube from the connecting hole into the connection channel;
    an electrical connection driving part, installed in the main body, and having a plurality of first electrical connection points correspondingly disposed in the connection channel;
    an electrical connection identification part, installed in the main body and configured to be adjacent with the electrical connection driving part, and the electrical connection identification part having a plurality of second electrical connection points correspondingly disposed in the connection channel;
    an organ identification unit, installed in the main body and telecommunicatively coupled to the electrical connection identification part, and the organ identification unit having an organ comparison table stored therein, wherein when the endoscope tube is inserted from the connecting hole into the connection channel, the endoscope tube and the plurality of first electrical connection points are electrically conducted with each other to generate a driving signal, and the endoscope tube and a part or all of the second electrical connection points are electrically conducted with each other to generate a type signal; and the organ identification unit compares the type signal received with the organ comparison table to determine the organ type corresponding to the endoscope tube, and output an execution signal accordingly; and
    a processing unit, installed in the main body and telecommunicatively coupled to the organ identification unit and the electrical connection driving part, such that after the execution signal and the driving signal are received, a result image is displayed according to the execution signal, wherein
    the plurality of first electrical connection points comes with a quantity of three, and the plurality of second electrical connection points comes with a quantity of four, and the driving signal is a binary 3-bit code, and the type signal is a binary 4-bit code, wherein the driving signal has a code of 111, the type signal has a code with a bit code of 1 corresponding to the second electrical connection point in a conducted status and a bit code of 0 corresponding to the second electrical connection point in a non-conducted status, and the organ comparison table comprises a plurality of encoded data and a plurality of organ data to facilitate the organ identification unit to read and compare the code of the type signal with the plurality of encoded data to obtain the corresponding organ data, so as to generate the execution signal.

2. The endoscope host according to claim 1, wherein the organ identification unit further comprises an organ tube identification mode and stores an organ tube comparison table, and in the organ tube identification mode, the organ identification unit compares the type signal received with the organ tube comparison table to determine an organ tube type corresponding to the endoscope tube and output an examined image signal according to the organ tube type; and the processing unit stores a plurality of endoscopic imaging modes, such that after the examined image signal is received, the corresponding endoscopic imaging mode is executed to display the image photographed by the endoscope tube.

3. The endoscope host according to claim 2, wherein the organ tube identification mode detects any two selected from the group consisting of colon probe, duodenum probe, colon probe, sigmoid colon probe, bronchus probe, small intestine probe, ureter probe, bladder probe, bronchus probe, nose and throat probe, gallbladder probe, and joint probe.

4. The endoscope host according to claim 3, wherein the organ identification unit stores a plurality of image clarity parameters corresponding to the organ type of the endoscope tube, and when the endoscope tube is applied for joint examination, the image clarity parameter falls within a range of 5~35 mm; when the endoscope tube is applied for stomach examination, the image clarity parameter falls within a range of 5~100 mm; when the endoscope tube is applied for vaginal examination, the image clarity parameter falls within a range of 15~50 mm; when the endoscope tube is applied for bronchial and bladder examination, the image clarity parameter falls within a range of 3~50 mm; when the endoscope tube is applied for colon examination, the image clarity parameter falls within a range of 2~100 mm; when the endoscope tube is applied for abdominal cavity examination, the image clarity parameter falls within a range of 15~120 mm; and when the endoscope tube is applied for duodenal examination, the image clarity parameter falls within a range of 4~90 mm.

5. The endoscope host according to claim 4, wherein a portion of the connection channel corresponding to the electrical connection driving part and the electrical connection identification part are crescent tubular grooves, such that when the connection channel is inserted with the endoscope tube, an arc contact area relative to the endoscope tube is formed, and the larger a diameter of the endoscope tube, the larger the area of the arc contact area; and the electrical connection identification part further comprises a signal path identification confirmation key disposed corresponding to an end of the connection channel, and after the signal path identification confirmation key is pressed by the endoscope tube and electrically conducted, the plurality of first electrical connection points and the plurality of second electrical connection points can be electrically conducted with the endoscope tube.

6. The endoscope host according to claim 5, wherein the main body comprises an imaging adjustment unit telecommunicatively coupled to the endoscope tube and the organ identification unit, and provided for adjusting distance between a lens of the endoscope tube and an imaging sensing element by linearly displacing either one of the lens and the imaging sensing element according to the image clarity parameter to produce clear images; wherein the endoscope tube further comprises a screw and a corresponding thread element, and the corresponding thread element is installed to a thread groove formed on the screw, and the corresponding thread element is coupled to the lens, such that the imaging adjustment unit can be rotated by the screw to move the lens forward or away from the imaging sensing element.

7. The endoscope host according to claim 5, wherein the main body comprises an imaging adjustment unit telecommunicatively coupled to the endoscope tube and the organ identification unit, and provided for adjusting distance between a lens of the endoscope tube and an imaging sensing element by linearly displacing either one of the lens and the imaging sensing element according to the image clarity parameter to produce clear images; wherein the endoscope tube further comprises a screw and a corresponding thread element, and the corresponding thread element is installed to a thread groove formed on the screw, and the corresponding thread element is coupled to the imaging sensing element, such that the imaging adjustment unit can be rotated by the screw to move the lens forward or away from the imaging sensing element.

8. An endoscope device for intelligently detecting organs, comprising:

an endoscope tube, having a shooting end and a connecting end configured to be relative to each other, and the connecting end having a plurality of third electrical connection points and at least one fourth electrical connection point, and the plurality of third electrical connection points and the fourth electrical connection point are arranged in a linearly vertical manner; and an endoscope host according to claim 6, wherein the plurality of first electrical connection points and the plurality of second connection points are arranged in a linearly vertical manner, and when the connecting end of the endoscope tube is inserted into the connecting hole, the plurality of third electrical connection points and the plurality of first electrical connection points are electrically conducted, and the fourth electrical connection point and one of the second electrical connection point are electrically conducted.

9. The endoscope device according to claim 8, wherein the endoscope tube has a casing and a circuit board, and the plurality of third electrical connection points and the fourth electrical connection point are disposed on the circuit board, and the casing is sheathed on an outer side of the circuit board and has a plurality of holes, such that the plurality of third electrical connection points and the fourth electrical connection point are exposed.

10. The endoscope device according to claim 9, wherein when the endoscope tube is applied for stomach examination, the diameter of the endoscope tube falls within a range of 9~11.4 mm; when the endoscope tube is applied for duodenal examination, the diameter of the endoscope tube falls within a range of 10.8~12.5 mm; when the endoscope tube is applied for colon examination, the diameter of the endoscope tube falls within a range of 12.9~13.7 mm; when the endoscope tube is applied for sigmoid colon examination, the diameter of the endoscope tube falls within a range of 12.8~13.2 mm; when the endoscope tube is applied for intestinal examination, the diameter of the endoscope tube falls within a range of 10.5~11.7 mm; when the endoscope tube is applied for bronchial examination, the diameter of the endoscope tube falls within a range of 5.7~6 mm; when the endoscope tube is applied for ureteral examination, the diameter of the endoscope tube falls within a range of 2.8~3.3 mm; when the endoscope tube is applied for bladder examination, the diameter of the endoscope tube falls within a range of 5.4~5.5 mm; when the endoscope tube is applied for nose and throat examination, the diameter of the endoscope tube falls within a range of 2~5 mm; when the endoscope tube is applied for biliary tract examination, the diameter of the endoscope tube falls within a range of 2.8~5.2 mm; when the endoscope tube is applied for chest examination, the diameter of the endoscope tube is 7 mm; and when the endoscope tube is applied for intubated throat examination, the diameter of the endoscope falls within a range of 4.1~5.2 mm.

11. The endoscope device according to claim 10, wherein when the endoscope tube has a diameter falling within a range of 2~5 mm, the endoscope tube has a hardness falling within a range of Shore 50~80 A, and the endoscope tube is provided for guiding and changing a nasogastric tube, and after the endoscope tube is passed and installed into the nasogastric tube by an exposed end disposed outside a human body and extended to an end of nasogastric tube placed in a human stomach, the nasogastric tube is withdrawn along the endoscope tube, and then another nasogastric tube is sheathed on the connecting end of the endoscope tube, so as to allow the nasogastric tube to be inserted into the human body along the endoscope tube for positioning.

12. The endoscope device according to claim 8, wherein the plurality of third electrical connection points and the fourth electrical connection point are configured with an interval apart from each other and in a protruding form, such that a depression is formed between any two adjacent third electrical connection points and the fourth electrical connection point, wherein the plurality of third electrical connection points and the fourth electrical connection point have a surface roughness smaller than the surface roughness of the depression.

* * * * *